United States Patent [19]

Pellerin et al.

[11] Patent Number: 4,594,900
[45] Date of Patent: Jun. 17, 1986

[54] AXIAL LOAD TESTING MACHINE

[75] Inventors: Roy F. Pellerin, Pullman, Wash.;
William L. Galligan, Salem, Oreg.;
George F. Eberle, St. Louis, Mo.

[73] Assignee: Washington State University Research Foundation, Inc., Pullman, Wash.

[21] Appl. No.: 727,265

[22] Filed: Apr. 25, 1985

[51] Int. Cl.⁴ ............................................ G01N 3/10
[52] U.S. Cl. ...................................... 73/806; 73/825; 73/837
[58] Field of Search ................. 73/826, 828, 830, 831, 73/837, 857, 794, 796, 798, 806, 825

[56] References Cited

U.S. PATENT DOCUMENTS

| | | | |
|---|---|---|---|
| 2,831,342 | 4/1958 | Adler et al. | 73/826 |
| 3,487,680 | 1/1970 | Eichenbrenner et al. | 73/857 X |
| 3,530,709 | 9/1970 | Nemeth | 73/837 X |

Primary Examiner—Jerry W. Myracle
Attorney, Agent, or Firm—Wells, St. John & Roberts

[57] ABSTRACT

Disclosed is a testing machine for testing specimens such as lumber which may have varying overall lengths. The testing machine includes the frame having an elongated longitudinal member which can be pivotally mounted with respect to stands. Two sets of transverse arms are connected to the longitudinal member at appropriate points. One set of transverse arms is pivotable. The transverse arms extend outwardly from the longitudinal member and have an extendible and contractible force member for increasing and decreasing the distance between the arms along one side of the frame. Jaw sets are pivotally mounted to the transverse arms opposite from the force member for engaging a specimen being tested. The jaw sets are preferably hydraulically closed, using the same hydraulic supply as used to extend the force member, thus automatically proportioning the gripping force of the jaws with relationship to the applied load to the specimen. The force member is provided with a load cell or other force transducer which continuously reads the force existing within the force member and applied to the test specimen. A closed loop feedback system compares the output of the forced transducer to a preprogrammed load function to provide a control signal used to adjust fluid supply to the force member and jaw sets.

21 Claims, 9 Drawing Figures

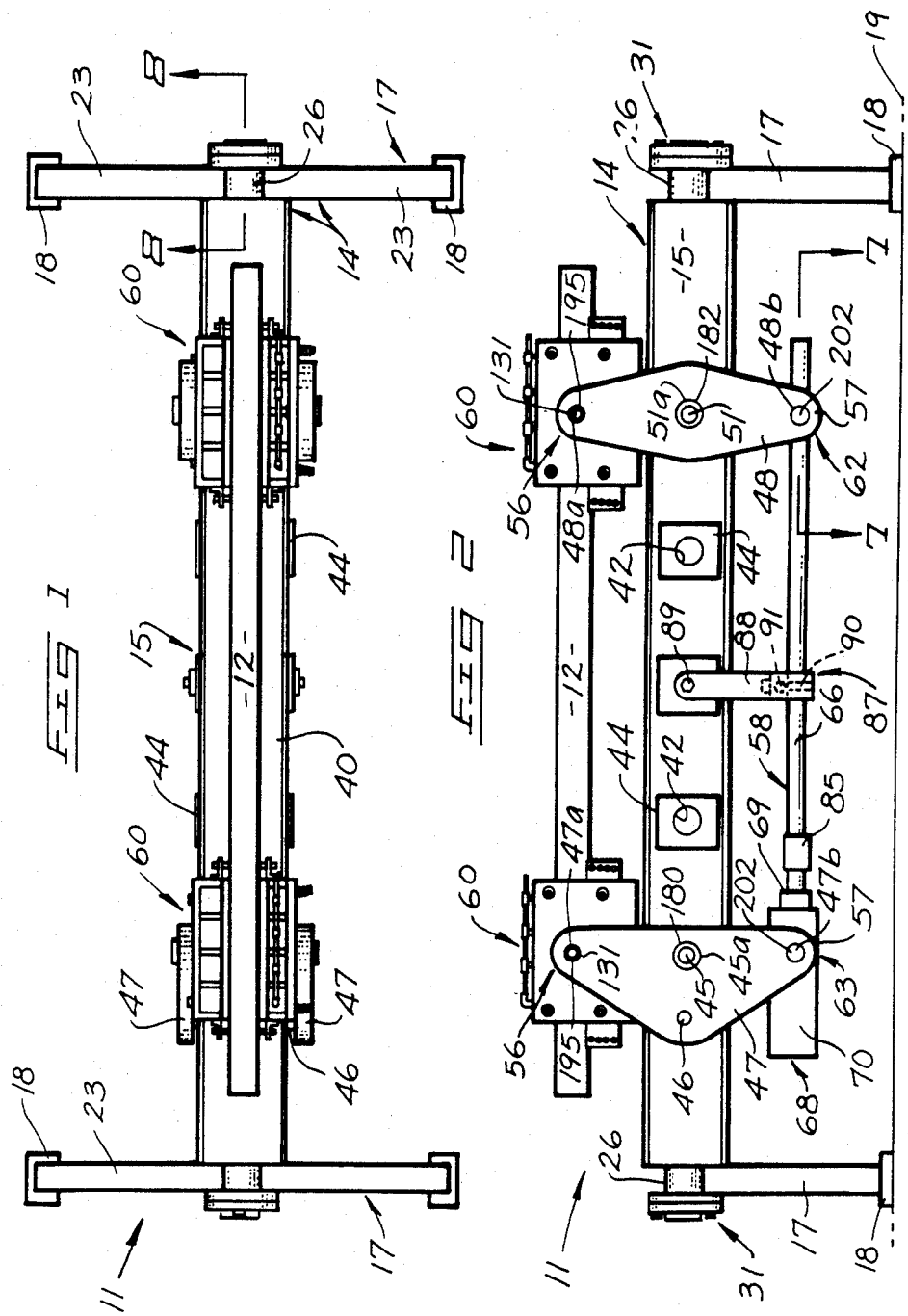

AXIAL LOAD TESTING MACHINE

TECHNICAL FIELD

The technical field of this invention is testing machinery for applying tensile or compressive forces to elongated members such as lumber and similar materials.

BACKGROUND OF THE INVENTION

Lumber is a product of nature having a variety of grain structures and discontinuities which significantly affect the strength of each particular lumber piece. In order to classify lumber according to the varying strength of each piece the lumber industry has developed grading criteria which are helpful at predicting strength ranges into which a piece of lumber should be sorted. Grading of lumber has typically been accomplished visually by noting the frequency, placement and size of discontinuities such as knots and separations. Such visual grading techniques are not sufficient to provide an accurate indication of strength for any particular piece. They do provide a general average strength value and range of strength values which can be used in engineering.

Grading of lumber has been more recently improved using a technique called mechanical stress rating of lumber. Such technique applies a flexural load to a piece of lumber. The flexural properties of the lumber piece are then analyzed to predict strength and appropriately grade the piece of lumber. Unfortunately, the accuracy of determining strength using mechanical stress rating techniques is still limited since it attempts to predict lumber strength from non-strength information, namely, flexure. Lumber graded in this manner still shows variability in strength which must necessarily be accommodated in determining allowable design limits.

The current invention is designed to apply a test or proof load which the lumber piece must withstand. This technique increases the design assurance over prior art grading techniques by providing lumber which is known to have passed a given applied load.

SUMMARY OF THE INVENTION

It is an object of this invention to provide a testing machine for applying axial tensile or compressive forces to elongated specimens without applying substantial bending moments or other nonaxial forces.

It is another object of this invention to provide a testing machine which allows varying lengths of specimens to be engaged and held in tension or compression without adjustment of the testing machine It is a further object of this invention to provide means which positively engage test specimens in tension or compression without unnecessarily compressing the specimen at the point of gripping or engagement.

It is another object of the invention to provide a testing machne which can be loaded with a specimen in a lateral manner.

It is a still further object of this invention to provide a testing machine which allows force applied to a test specimen to be controlled using a closed loop feedback control system which senses the force applied by the machine.

These and other objects, advantages and benefits of the invention will be apparent from the description given herein.

BRIEF DESCRIPTION OF THE DRAWINGS

The invention is illustrated in the accompanying drawings, in which:

FIG. 1 is top view of a preferred testing machine according to this invention;

FIG. 2 is a side elevational view of the testing machine shown in FIG. 1;

DETAILED DESCRIPTION OF THE PREFERRED EMBODIMENT

Figure 3:
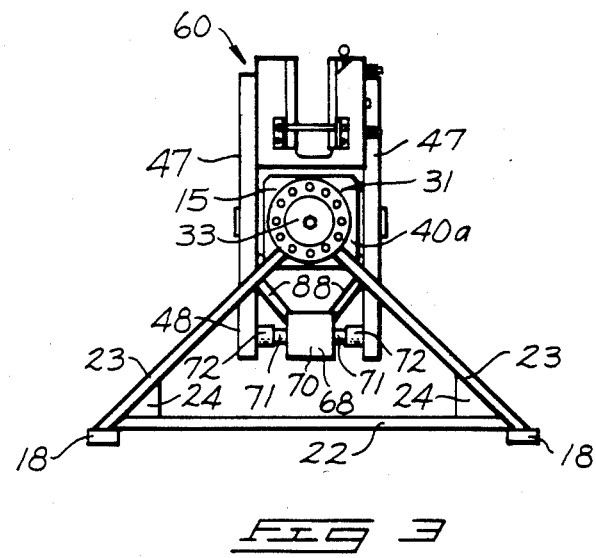
FIG. 3 is an end elevational view of the testing machine shown in FIG. 1.

In compliance with the constitutional purpose of the Patent Laws "to promote the progress of science and useful arts" (Article 1, Section 8), applicant submits the following disclosure of the invention.

FIGS. 1 and 2 show a preferred embodiment testing machine 11 according to this invention. Testing machine 11 is specifically designed to proof load elongated test specimens such as lumber piece 12 shown in FIGS. 2 and 5. Forces applied to lumber piece 12 by testing machine 11 are axial tensile forces or axial compressive forces without any substantial application of bending moments or shear forces other than those induced within the structure of the specimen in response to the applied axial forces.

Testing machine 11 includes a frame 14. Frame 14 includes an elongated longitudinal member 15. Longitudinal member 15 can be supported by any suitable means such as A-frame end stands 17 which are positioned at each end of longitudinal member 15. Stands 17 can be used to support member 15 upon floor 19 or other substantially horizontal surface, or alternatively can be used to cantilever or otherwise hang member 15 from a wall, ceiling or other supporting structure (not shown).

A-frame stands 17 preferably comprise two foot pieces 18 which rest upon floor 19 or other supporting surface. Stands 17 further advantageously include transverse members 22 (FIG. 3) extending between foot pieces 18 and angled members 23 connected to foot pieces 18 and transverse members 22. Gusset plates 24 can be provided to further reinforce the connection between angled members 23 and transverse members 22.

A-frame stands 17 also preferably include collars 26 for rotatably supporting longitudinal member 15 therein. Collars 26 are advantageously positioned at the juncture of angled members 23. Collar 26 (see FIG. 8) has a cylindrical aperture 27 extending therethrough to act as a bearing surface for supporting journals 29 formed at or near the ends of longitudinal member 15. Such construction allows journals 29 to rotate within collar 26 so that longitudinal member 15 can be pivoted about its longitudinal axis into various angular positions.

Figure 8:
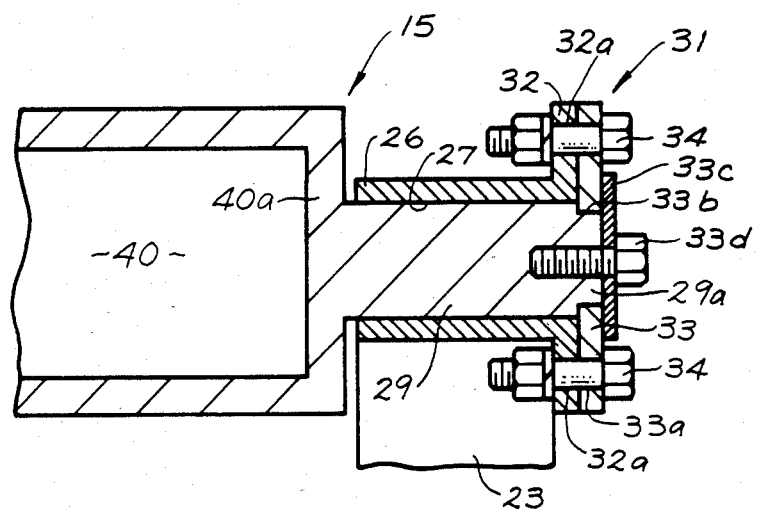
FIG. 8 is an enlarged partial side sectional view taken along line 8—8 of FIG. 1.

The relative angular position or longitudinal member 15 can be adjustably fixed using a suitable rotational securement means such as 31 shown in detail in FIG. 8. Rotational securement means 31 includes a fixed flange 32 which is nonrotatably mounted to or integral with collar 26. Flange 32 is annular and does not obstruct circular aperture 27. A pivoting plate 33 is nonrotatably mounted to the pivotable longitudinal member 15 adjacent to fixed flange 32 such as at the outer end of journals 29. Pivoting plate 33 can be nonrotatably connected to journal 29 using a variety of structures. FIG. 8 shows a square extension 29a received within a mating square aperture 33b in plate 33. A cover plate 33c is secured in place using bolt 33d.

Fixed flange 32 is provided with apertures 32a at appropriate angular positions about the flange, usually at equal radial distances from the longitudinal axis of longitudinal member 15. Pivoting plate 33 is also provided with apertures 33a passing therethrough usually at a plurality of angular positions about the plate and at approximately equal radial positions to each other and with respect to apertures 32a in fixed flange 32. Apertures 32a and 33a are aligned and bolts 34 are extended therethrough in order to secure the relative position therebetween, thereby fixing the angular position of longitudinal member 15.

Fixed flange 32 can advantageously be constructed with apertures 32a having equal angular positions about the flange such as at ten different angular positions, each having an approximate angular spacing of 36° of arc. Pivoting plate 33 can advantageously be constructed with apertures 33a also being at equal angular positions thereabout but with different angular spacing than used with fixed flange 32. A suitable number of apertures 33a is 12 at angular increments of approximately 30° of arc. By having the angular spacing of apertures 32a different from apertures 33a it is possible to fix member 15 at smaller incremental angular positions such as 6 degrees of arc for 10 and 12 holes for apertures 32a and 33a. Various numbers of apertures 32a and 33a can be used to provide the desired number and spacing of angular orientations for longitudinal member 15. Alternatively, a continuously adjustable means (not shown) can be provided for fixing the angular position of member 15 with respect to remaining portions of frame 14 at any desired orientation.

Longitudinal member 15 is preferably constructed with a beam portion 40 extending between journals 29. Beam portion 40 is advantageously constructed using a hollow tubular member such as the square tubular member shown in FIGS. 1, 2 and 3. End plates 40a are provided at the ends of beam portion 40 to connect journals 29 thereto. Beam portion 40 is provided with a plurality of beam apertures 42 extending therethrough at appropriately spaced positions along longitudinal member 15. Beam portion 40 is advantageously reinforced using reinforcement plates 44 through which apertures 42 extend.

Testing machine 11 further includes two sets of transverse arms such as first or proximal arms 47 and second or distal arms 48. Proximal arms 47 are nonrotatably mounted upon opposite sides of longitudinal member 15 using a transverse shaft 45 and anti-rotation pin 46 which extends through longitudinal member 15. Shaft 45 extends through beam apertures 42 and apertures 45a formed in arms 47. Suitable bearing means 180 are provided between shaft 45 and apertures 45a to minimize friction. Tapered roller bearings can advantageously be used as bearings 180 to eliminate clearance. Bearing covers (not shown) can be included to exclude dust.

Distal arms 48 are pivotally mounted upon opposite sides of longitudinal member 15 using a transverse shaft 51 which extends through beam apertures 42 and through apertures 51a formed in arms 48. Suitable bearing means 182, such as tapered roller bearings, are provided between shaft 51 and apertures 51a. Dust covers (not shown) are also preferably included. Distal arms 48 can be positioned at any appropriate aperture 42 depending upon the length over which the specimen is to be tested.

Arms 47 and 48 extend transversely outward, each having specimen ends 56 and force member ends 57. First and second jaw sets 60 are pivotally connected to specimen ends of arms 47 and 48 at pivots 47a and 48a, respectively. An extendible and contractible force member 58 extends between and is pivotally attached to arms 47 and 48 at pivots 47b and 48b, respectively at force member ends 57.

Force member 58 is pivotally connected to distal arms 48 at pivot 48b by a pivot connection assembly 62. Force member 58 is also pivotally connected to proximal arms 47 at pivot 47b by pivot connection assembly 63. Force member 58 advantageously includes an elongated rod 66 which extends between pivot connection assembly 62 and a hydraulic or pneumatic ram 68, also forming a part of force member 58.

Ram 68 includes an extendible piston 69 which allows the length of force member 58 between transverse arms 47 and 48 to be extended and contracted. Ram 68 also includes an exterior casing 70. Exterior casing 70 can be fitted with stub shafts 71 which extend within pivot collars 72 which are rigidly attached to force member ends 57 of pivot arms 47. Pivot collars 72 have apertures 73 extending thereinto for pivotally receiving stub shafts 71 therein. This arrangement comprises pivot connection assembly 63.

Figure 7:
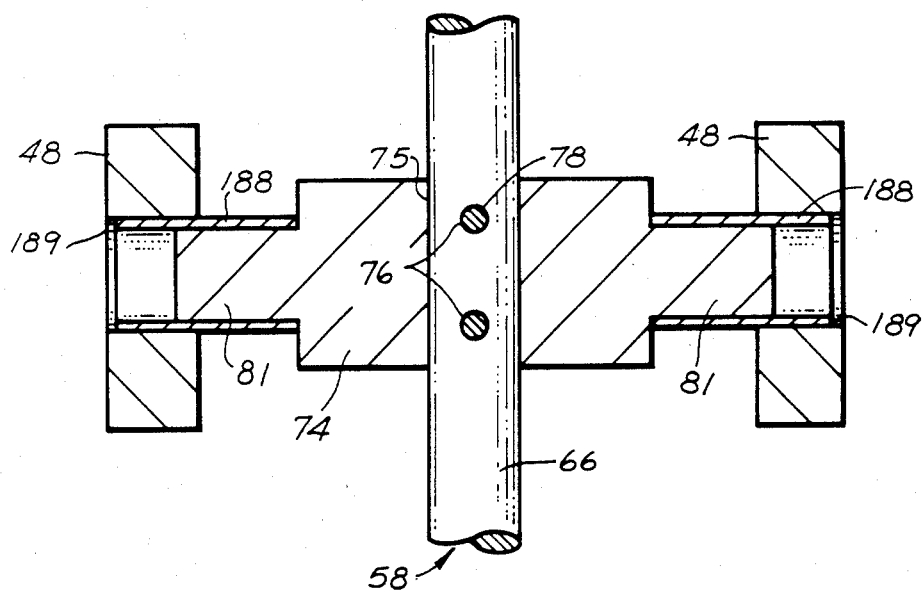
FIG. 7 is an enlarged partial sectional view taken along line 7—7 of FIG. 2, showing a suitable connection pin mechanism used in the testing machine shown in FIG. 1.

Distal pivot arm connection assembly 62 is shown in detail in FIG. 7 and includes arms 48 on opposite sides of rod 66. Connection block 74 is provided with an aperture 75 through which elongated rod 66 extends. Connection block 74 is connected to rod 66 by extending suitable connectors such as tapered drift pins 76 through apertures in block 74 and further through apertures 78 formed through rod 66.

Force member 58 is also preferably provided with an electronic in-line load cell or other force transducer 85 thereby providing continuous accurate information of the actual force existing within force member 58. Load cell or force transducer 85 is preferably a bidirectional device capable of measuring either compressive or tensile force existing within member 58. Force transducer 85 provides an electronic output signal indicative of the quantity and direction of the force existing within member 58.

Testing machine 11 is advantageously provided with an intermediate support 87 for helping to vertically support force rod 58. Intermediate support 87 is desirable when force member 57 is sufficiently long so that detectable deflection occurs within the member. Intermediate support 87 is advantageously constructed using two side brackets 88 which are pivotally mounted at an appropriate aperture 42, such as by extending a pivotable shaft 89 therethrough. A bolt or other fastener 90 extends through rod 66 and is connected to a cross piece 91. Cross piece 91 is pivotally connected to lower ends of side brackets 88. Intermediate support 87 is thus pivotable at the top and bottom thereof to allow force member 58 to be satisfactorily supported without applying axial force, bending moments or shear forces to member 58. Other suitable supports can also be used.

Figure 4:
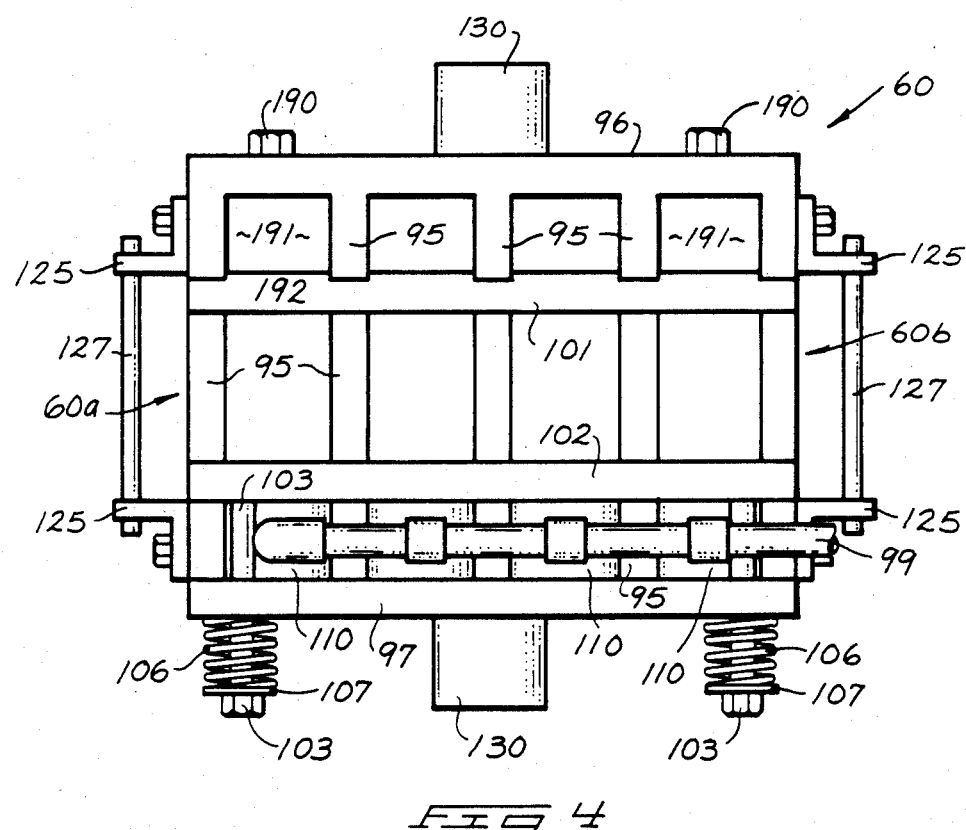
FIG. 4 is an enlarged isolated top view of one jaw set used in the invention of FIG. 1.
Figure 5:
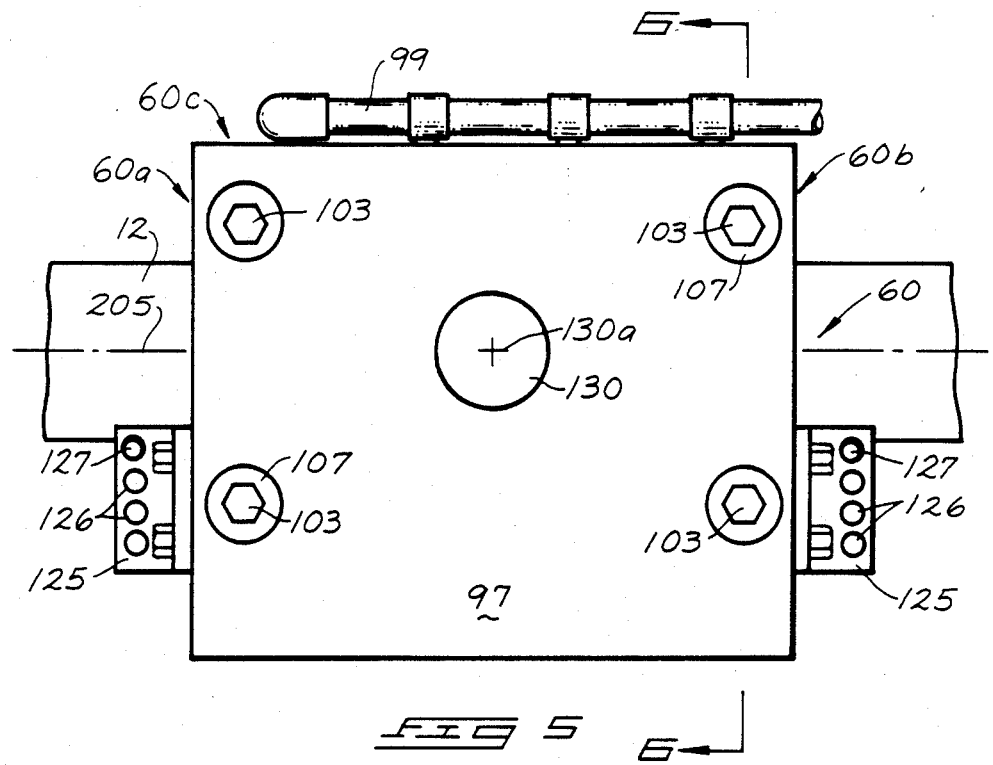
FIG. 5 is a side elevational view of the jaw set shown in FIG. 4.
Figure 6:
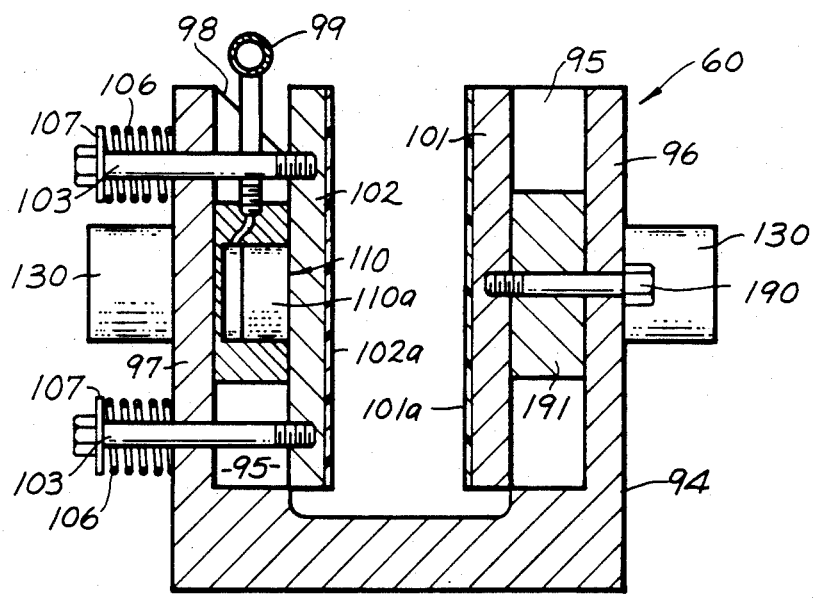
FIG. 6 is a cross-sectional view taken along line 6—6 of FIG. 5.

Testing machine 11 also includes means for engaging and holding specimens such as first and second jaw sets 60. First and second jaw sets 60 are shown in FIGS. 4–6 and preferably are constructed using U-shaped body assemblies 94. U-shaped body assemblies 94 can include a plurality of U-shaped pieces 95 which are welded or otherwise structurally attached to a first side plate 96 and a second side plate 97. U-shaped pieces 95 are advantageously beveled along surfaces 98 to facilitate placement of hydraulic supply lines 99.

Jaw sets 60 further include a stationary jaw piece 101 and a movable jaw piece 102. Stationary jaw piece 101 can advantageously be detachably mounted using bolt 190. Stabilizing blocks 191 fit between adjacent U-shaped pieces 95 to secure the longitudinal position of jaw piece 101. Grooves 192 in the back of stationary jaw piece 101 can also be provided to help secure the longitudinal position of jaw piece 101.

Movable jaw piece 102 is transversely movable toward and from stationary jaw piece 101 thereby allowing specimens such as 12 to be clamped therebetween. An expanded position of piece 102 is indicated in FIG. 6. Contracted positions vary depending upon the thickness of the specimen clamped therein and the contraction travel for which jaw sets 60 are designed. A fully contracted position can be provided which allows jaw piece 102 to contact 101. However, such full contraction capability is not illustrated.

Guide rods 103 are provided at appropriate locations such as the four locations shown in FIG. 5 in order to position movable jaw piece 102 against longitudinal and vertical displacement. Guide rods 103 are rigidly attached to movable jaw piece 102 and extend outwardly from the back of jaw piece 102 and through apertures 105 formed in plate 97. Guide rods 103 can extend outwardly and have biasing springs 106 positioned thereabout restrained between plate 97 and a retaining cap 107 mounted on the end of guide rods 103. Retaining cap 107 can advantageously be an appropriately sized washer. Springs 106 bias movable jaw piece 102 away from stationary jaw piece 101 and into an expanded position contacting U-shaped pieces 95.

Jaw pieces 101 and 102 can be constructed in a variety of different shapes along contacting surfaces 101a and 102a. Contacting surfaces 101a and 102a are preferably planar, parallel and lined with a high density polyurethane preferably used with lumber, or alternative materials exhibiting a high coefficient of friction with the specimens being tested. Alternatively, shaped contacting surfaces with or without engagement means (not shown) are also possible.

Movable jaw pieces 102 are contracted inwardly toward stationary jaw piece 101 using a plurality of hydraulic, pneumatic or other actuators 110. Actuators 110 are advantageously thin profile hydraulic cylinders which are supplied with pressurized hydraulic fluid through lines 99. Actuators 110 increase in transverse dimension by extending piston 110a to force movable jaw piece 102 towards stationary jaw piece 101.

The total hydraulic cross-sectional area of actuators 110 for each jaw set 60 is preferably equal to some appropriate multiple greater than 1.0 times the hydraulic cross-sectional area of force member ram 68. A suitable area ratio for lumber with polyurethane contacting surfaces 101a and 102a has been found to be 1.1. Such area ratios create a gripping force which varies in direct proportion with the axial force applied through member 58 to specimen 12. The gripping force thus is automatically increased as the axial force applied to the specimen is increased, thus securely holding the specimen at each end and preventing unnecessary gripping force from permanently compressing or damaging the specimen. This is particularly important when the invention is used as a proof loading test machine for lumber or other soft materials so that individual pieces of lumber being proof tested are not damaged by excessive gripping force.

Jaw sets 60 are open along three surfaces through which specimen 12 can extend. The open surfaces can be described as ends 60a and 60b and entry face 60c. Such construction allows easy loading of specimen 12 and allows overlength specimens of varying length to be accommodated.

Jaw sets 60 are further provided with positioning brackets 125 at each end of body pieces 94 (FIG. 4). Positioning brackets 125 are provided with apertures 126 (FIG. 5) through which support rods 127 can extend. Apertures 126 are vertically located in brackets 125 so that the neutral axis 205 of test specimen 12 resting upon support rods 127 is aligned with the transverse pivot axes 130a of jaw sets 60. This allows a purely axial tensile or compressive load to be applied to the specimen without applying significant bending moments or shear forces. Apertures 126 can be formed in brackets 125 so as to easily and properly position appropriate sizes of test specimens. In the case of lumber, nominal sizes such as 2×6, 2×8 and 2×10 can easily be tested by appropriately positioning the apertures 126 for proper alignment of the neutral axes for such lumber sizes.

Jaw sets 60 further include trunnions 130 at opposite sides thereof. Trunnions 130 are cylindrical and aligned to define transverse pivotal axes which are perpendicular to the longitudinal axis of member 15. Trunnions 130 are received within suitable bearing means 195 fit within apertures 131 formed in specimen ends 56 of arms 47 and 48.

It is noteworthy that testing machine 11 is constructed to balance forces as nearly as possible. Transverse arms 47 and 48 are approximately equally spaced from the longitudinal axis of member 15 so that jaw sets 60 are suspended therebetween supported at both sides. Similarly, force member 58 is approximately centered between arms 47 and 48 in order to balance forces applied by force member 58 to arms 47 and 48. Specimen 12 is preferably aligned above the longitudinal axis of member 15 so that balanced forces are transferred by arms 47 and 48 to jaws 60 and thus to specimen 12, thereby avoiding application of any lateral bending moments.

The transverse distances of lever arms 47 and 48 between the axes of shafts 45 and 51 to the pivot axes 130a of jaw sets 60 and pivot axes 202 of force member 58 are preferably made equal in order to balance the forces developed in force member 58 and specimen 12. Equal transverse lever arms simplifies using the invention since measurement of the force in member 58 using force transducer 85 is also measurement of the load applied to specimen 12. Alternative leverages are workable with modification of the transverse arms 47 and 48 and compensation for the change in force transducer output.

Figure 9:
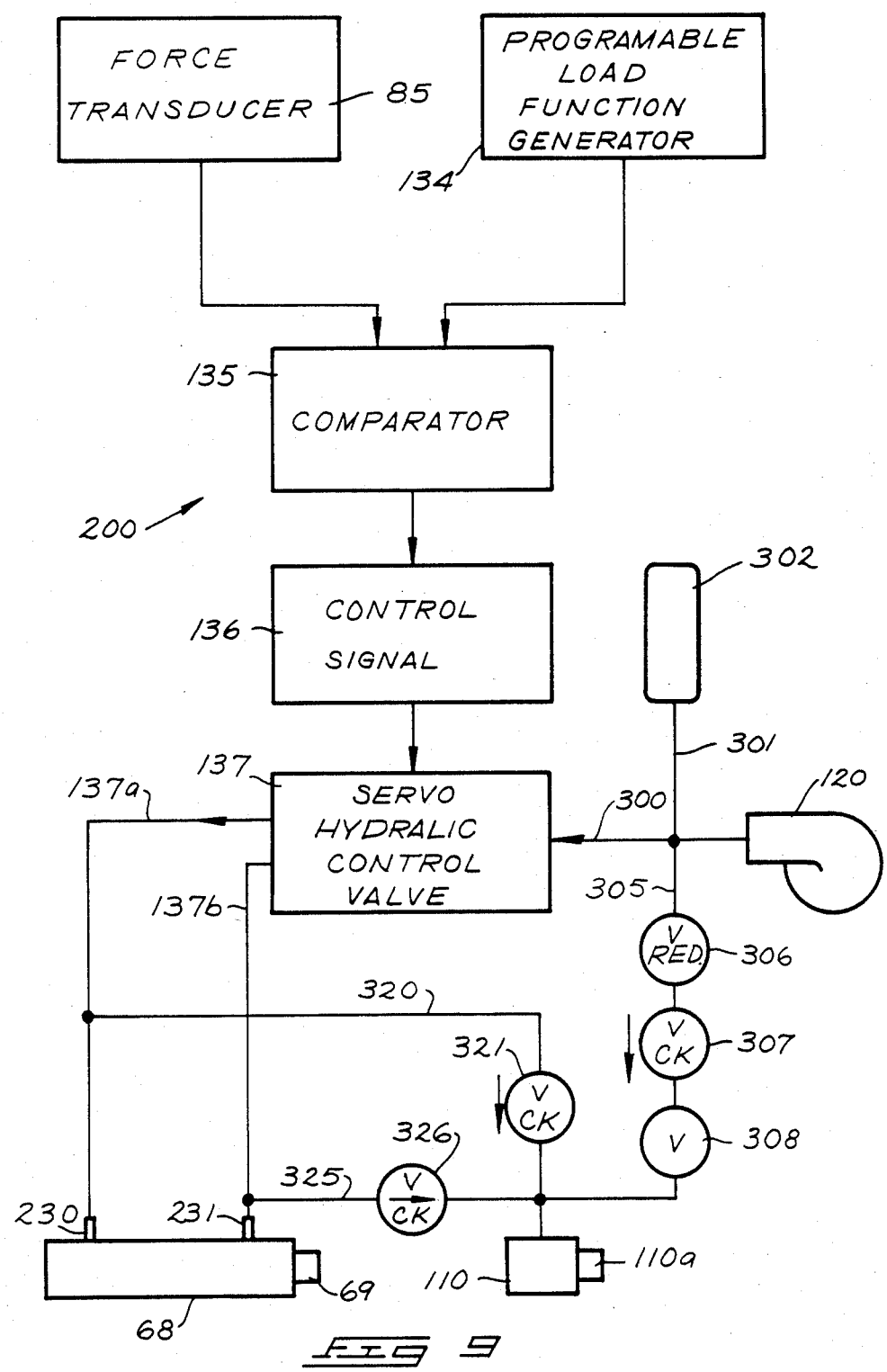
FIG. 9 is a schematic view of a control system used to operate the testing machine of FIG. 1.

FIG. 9 shows a schematic diagram of a control system 200 which is advantageously used for controlling testing machine 11. Control system 200 includes force transducer 85 which is connected directly to or forms a part of force member 58 thereby giving an accurate, continuous measure of the force existing within member 58 and the applied force on specimen 12. A programmable load function generator 134 is used to provide an appropriate preprogrammed load function signal. Typical load function signals are typically ramp functions increasing linearly from zero at rates in the range of 200 to 1,000 lbs. force per minute. Many alternative load functions are also possible depending upon the specific type of testing and material being tested.

The output signals from force transducer 85 and load function generator 134 are compared electronically in a comparator 135. the resulting output is a control signal 136 which can be amplified or otherwise electronically conditioned to appropriately control a servo hydraulic control valve 137. Valve 137 is preferably a singular distributional flow control valve having an extension output 137a and a contraction output 137b. The flow quantity and whether supplied to output 137a or 137b is dependent upon the control signal 136.

Pressurized fluid is supplied from pump 120 or other suitable pressurized fluid supply to valve 137 through outflow line 300. Line 300 is provided with a branch line 301 which is connected to a fluid accumulator 302 and which evens the flow supplied to valve 137. Another branch line 305 is connected to line 300 and is provided with a pressure reducing valve 306, check valve 307, and manual or solenoid operated valve 308. Valve 308 is used to initially supply actuators 110 with reduced pressure fluid for closing jaw sets 60 upon specimen 12 before application of an axial load.

The extension and contraction outputs 137a and 137b are connected to extension and contraction fittings 230 and 231, respectively of force member ram 68. Pressurized fluid entering extension fitting 230 extends ram piston 69. Pressurized fluid entering contraction fitting 231 retracts piston 69. Ram 68 is thus extended or retracted to apply compressive or tensile loads upon specimen 12, respectively.

Branch line 320 is connected to the extension output 137a of valve 137 and provided with a suitable check valve 321 to prevent backflow. Another branch line 325 is connected to the contraction output 137b of valve 137 and also provided with check valve 326. Outflow through check valves 321 and 326 cause actuators 110 to extend thus gripping specimen 12 in jaw sets 60. Fluid supplied through valve 308 also cause gripping of the specimen until pressurized fluid in lines 320 or 325 exceed the presure output from valve 308. When such occurs, the jaw sets are automatically provided with gripping force proportional to the applied axial load on specimen 12.

The manner of using the invention will now be described.

Testing of specimen 12 begins with hydraulic control valve 137 and valve 308 closed, thereby reducing the hydraulic pressure to ram 68 and actuators 110 to zero. This places jaw set 60 in an expanded position with movable jaw piece 102 spaced fully from stationary jaw 101. Jaw sets 60 are open along three surfaces so that overlength test secimens can be easily inserted therein by sliding endwise, or preferably, laterally thereinto either from above, from the side, or in some other suitable direction with the longitudinal member 15 and jaw set 60 oriented in the desired angular position for easy positioning of the specimen to within the jaws.

Support rods 127 are appropriately positioned within apertures 126 of brackets 125 so that the neutral axis of the specimen is aligned with the pivotal axes 130a defined by trunnions 130.

An operator initiates testing by opening valve 308 to grip specimen 12 in jaw sets 60. The programmable load function generator 134 is then initiated into operation and the desired load function is commenced. This produces a control signal 136 demanding increased hydraulic flow which is fed to force member ram 68 and jaw set actuators 110 simultaneously. Pressurized hydraulic fluid is supplied either to extension fitting 230 to extend piston 69, or alternatively, to contraction fitting 231 to retract piston 69. When piston 69 is extended, force member 58 is placed in compression. The compression existing within force member 58 is transferred through arms 47 and 48 and applied to specimen 12, thereby creating a compression load upon specimen 12. Specimen 12 can also be tested in tension by retracting piston 69 into ram 68 thus shortening force member 58 and thereby placing specimen 12 in tension.

Force applied by force member 58 is increased or decreased according to the programmed load function generator 134 at the desired rate. Comparator 135 rapidly assesses the actual force existing within member 58 using an output signal from force transducer 85 and comparing it against the programmed load function. Any deviation from the programmed load causes a control signal 136 to adjust hydraulic control valve 137 thereby increasing the fluid flow and pressure available to ram 68 and actuators 110. This operation continues until the programmable load function has either reached the breaking point of the specimen or reached a maximum point. If the specimen survives the maximum applied load then the preprogrammed load function typically returns the axial load back to zero force in a relatively quick period of time, for example, four times as fast as the loading function. This releases the load on the specimen. Valve 308 is then closed and movable jaw piece 102 returns into the expanded position. Specimen 12 can then be removed either by hand or by automated handling equipment (not shown). Testing machine 11 is thus ready for testing or proof loading another specimen.

Testing machine 10 can be adjusted for varying longitudinal spacing between jaw sets 60. This is accomplished by removing shaft 51 from bearings 182 and removing one or both of the pivot arms 48 from jaw set 60 and pivot connection assembly 62. The jaw set 60 is moved, preferably by rolling upon rollers (not shown) into location adjacent the new aperture 42 desired. The pivot arms 48 are assembled together upon shaft 51 and pivotally connected to the jaw set 60 at trunnions 130. Pivot connection assembly 62 is reconnected at a new position along force member rod 66 which has previously been provided with apertures through which pins 76 extend.

Testing machine 11 can be manufactured according to well known manufacturing, metal working, and other material working techniques in the configuration as shown and described, to perform the functions described.

In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims, appropriately interpreted in accordance with the doctrine of equivalents.

We claim:

1. A testing machine for testing axial load carrying ability of an elongate test specimen, comprising:
a frame;
at least one first transverse arm mounted nonrotatably upon said frame;
at least one second transverse arms pivotally mounted upon said frame at a location spaced from said first transverse arm;
a force member extending between and pivotally connected to said first and second transverse arms; said force member being adjustable in axial length to thereby pivot said second transverse arm upon said frame;
specimen engagement means pivotally mounted upon said first and second transverse arms for engaging said specimen and applying an axial load thereto; and
force transducer means for measuring the force applied to the specimen by said force member.

2. The testing machine of claim 1 wherein said frame is provided with a plurality of means for pivotally mounting said second transverse arm thereto, for allowing adjustment of the spacing between said first and second pivot arms.

3. The testing machine of claim 2 wherein said means for pivotally mounting said second transverse arm includes at least one shaft extending through apertures in said frame.

4. The testing machine of claim 1 wherein pivot axes of said specimen engagement means are spaced transversely outward a transverse lever arm distance equal to a transverse lever arm distance of said force rod.

5. The testing machine of claim 1 wherein said frame includes an elongate longitudinal member and ends stands connected thereto; said longitudinal member being adjustably mounted to said end stands to allow pivotal adjustment about a longitudinal axis.

6. The testing machine of claim 1 wherein there are a pair of first transverse arms mounted upon opposite sides of a longitudinal member forming a part of the frame, and a pair of second transverse arms mounted upon opposite sides of the longitudinal member.

7. The testing machine of claim 6 wherein:
said specimen engagement means are pivotally suspended between specimen ends of said pairs of first and second transverse arms; and
said force member is pivotally suspended between force member ends of said pairs of first and second transverse arms.

8. The testing machine of claim 7 wherein said force member comprises at least one pressurized fluid powered ram which is pivotally connected between a pair of transverse arms.

9. The testing machine of claim 6 wherein said specimen engagement means, comprises:
a U-shaped frame open along ends and an entry face;
a stationary jaw piece rigidly connected within the U-shaped frame;
a movable jaw piece mounted within the U-shaped frame in opposing relationship to said stationary jaw piece; said movble jaw piece being movable toward and from said stationary jaw piece; and
actuator means for forcing said movable jaw toward said stationary jaw piece.

10. The testing machine of claim 9 wherein the actuator means is powered by pressurized fluid also used to change the axial length of said force member, so that gripping force of said jaw means varies proportionally to the axial load applied by the force member.

11. The testing machine of claim 1 wherein said force member comprises at least one pressurized fluid powered ram.

12. The testing machine of claim 1 wherein said specimen engagement means comprises a U-shaped frame open along ends and an entry face;
and at least one movable jaw piece movably mounted to said U-shaped frame for contracting and engaging the test specimen therein.

13. The testing machine of claim 1 wherein said engagement means are jaw means having open ends which allow varying length specimens to be inserted thereinto.

14. A testing machine for testing axial load carrying ability of an elongate test specimen, comprising:
a frame having an elongate longitudinal member; said longitudinal member having a plurality of beam apertures;
a pair of first transverse arms nonrotatably mounted upon opposite sides of said longitudinal member;
a pair of second transverse arms detachably and pivotally mounted upon opposite sides of said longitudinal member at said beam apertures; said second transverse arms being longitudinally spaced from said first transverse arms;
a force member extending between and pivotally connected to said first and second transverse arms for controllably changing in axial length to thereby pivot said second transverse arms upon said longitudinal member;
first and second jaw means pivotally mounted upon said first and second transverse arms, respectively, opposite from said force member; said jaw means having expandable and contractible jaw pieces for contracting and gripping a test specimen placed therein; said jaw means being open along ends and entry face thereof; and
force transducer means for measuring the force applied to the specimen by said force member.

15. The testing machine of claim 14 wherein:
said jaw means are pivotally suspended between specimen ends of said pairs of first and second transverse arms; and
said force member is pivotally suspended between force member ends of said pairs of first and second transverse arms.

16. The testing machine of claim 15 further comprising automatic control system means for automatically controlling said force member to apply force in a desired manner.

17. The testing machine of claim 16 wherein said automatic control means is connected to receive information from said force transducer means for controlling application of force by the force member.

18. The testing machine of claim 14 wherein the frame further comprises at least one end stand connected thereto to support the longitudinal member in a desired location.

19. The testing machine of claim 18 wherein said longitudinal member is adjustably mounted to said end stand to allow pivotal adjustment about a longitudinal axis of the longitudinal member.

20. The testing machine of claim 14 wherein the force transducer is attached to said force member to directly measure the force applied thereby.

21. The testing machine of claim 20 wherein said jaw means comprises:

a U-shaped frame open along ends and an entry face;

a stationary jaw piece rigidly connected within the U-shaped frame;

a movable jaw piece mounted within the U-shaped frame in opposing relationship to said stationary jaw piece; said movable jaw piece being movable toward and from said stationary jaw piece; and actuator means for forcing said movable jaw toward said stationary jaw piece.

* * * * *